United States Patent [19]

Sudo et al.

[11] Patent Number: 4,665,331
[45] Date of Patent: May 12, 1987

[54] BRUSHLESS DC MICROMOTOR

[75] Inventors: Michio Sudo, Tokyo; Toshihiro Hotta, Kyoto; Minoru Imazato, Otsu, all of Japan

[73] Assignees: Kangyo Denkikiki Kabushiki Kaisha, Tokyo; Kabushiki Kaisha Morita Seisakusho, Kyoto, both of Japan

[21] Appl. No.: 821,245

[22] Filed: Jan. 22, 1986

[30] Foreign Application Priority Data

Feb. 1, 1985 [JP] Japan .................................. 60-18955

[51] Int. Cl.$^4$ ............................................. H02K 11/00
[52] U.S. Cl. ............................ 310/68 R; 310/40 MM; 310/156; 310/177; 310/184; 310/DIG. 6
[58] Field of Search ................... 310/42, 43, 45, 68 R, 310/71, 40 MM, 179, 180, 184, 198, 201, 208, 156, 259, DIG. 6, 177, 46, 73; 174/68.5; 433/27, 103, 131; 340/555-557; 357/19

[56] References Cited

U.S. PATENT DOCUMENTS

| | | | |
|---|---|---|---|
| 2,760,127 | 8/1956 | Duncan | 310/DIG. 6 |
| 2,885,645 | 5/1959 | Wennerberger | 310/DIG. 6 |
| 2,886,880 | 5/1959 | Eisler | 310/DIG. 6 |
| 4,039,875 | 8/1977 | Morreale | 310/DIG. 6 |
| 4,115,915 | 9/1978 | Godfrey | 310/180 |
| 4,151,433 | 4/1979 | Flick | 310/208 |
| 4,319,152 | 3/1982 | van Gils | 310/201 |
| 4,431,932 | 2/1984 | Nathenson | 310/208 |

FOREIGN PATENT DOCUMENTS

| | | |
|---|---|---|
| 1613380 | 9/1970 | Fed. Rep. of Germany ... 310/DIG. 6 |
| 0364026 | 10/1962 | Switzerland .................. 310/DIG. 6 |
| 1423866 | 2/1976 | United Kingdom ......... 310/DIG. 6 |
| 1440637 | 6/1976 | United Kingdom ......... 310/DIG. 6 |

Primary Examiner—R. Skudy
Attorney, Agent, or Firm—Koda and Androlia

[57] ABSTRACT

A brushless DC micromotor made up of a stator coil and a rotor housed inside thereof with magnet poles formed therein, which micromotor is characterized in that the stator coil is formed by coaxially winding more than one coil sheet formed on an insulating sheet, on which coil sheet a plurality of coil patterns are continuously provided in series in the direction of winding. The motor of the present invention can be made smaller, thinner and lighter than the conventional counterpart made by the use of a wound copper wire coil.

1 Claim, 11 Drawing Figures

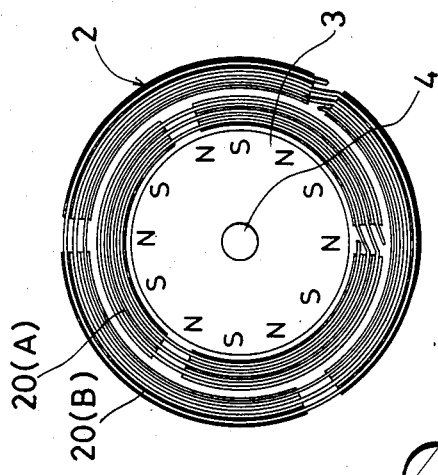
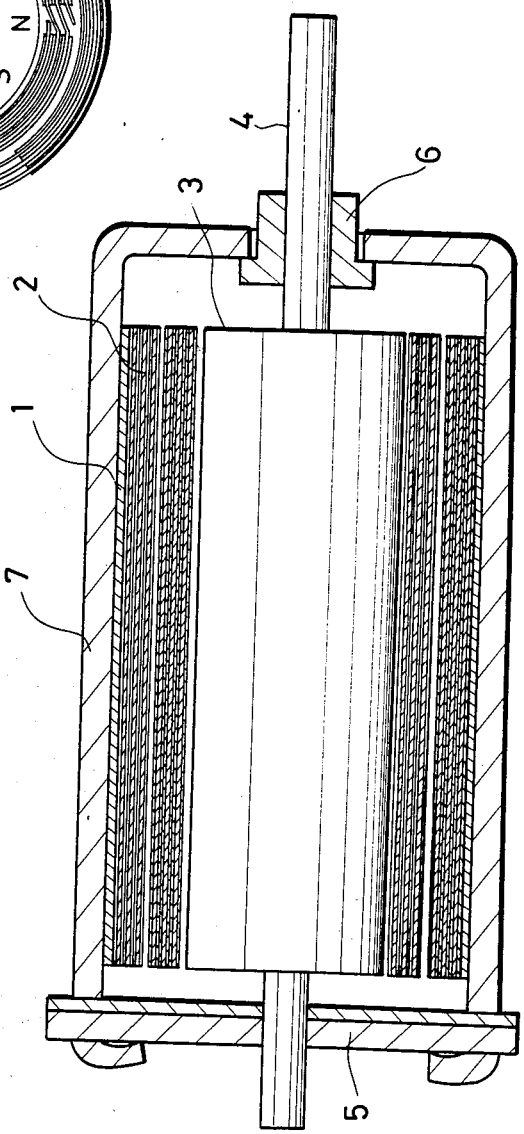
FIG. 2
FIG. 1

BRUSHLESS DC MICROMOTOR

BACKGROUND OF THE INVENTION

1. Field of the Invention

The present invention relates to a brushless DC micromotor.

2. Prior Art

Hitherto micromotor of this kind has used to have its stator coil formed by winding an insulated copper wire such as enameled wire, hence the stator coil used to be large in size and thick, this badly interfering with micromotor's miniaturization.

When a micromotor is made by the use of a stator coil formed by winding such an insulated copper wire, generally the ratio of the volume of the coil conductor per unit space is reduced, this resulting in lowering of the motor's efficiency, and it is then extremely difficult to manufacture a midget micromotor improved in efficiency.

Moreover, a micromotor using the stator coil as mentioned above is made by first forming the coil by winding the enameled wire and then inserting it into a yoke and bonding therein, this resulting in a poor workability and giving rise to a serious problem of the enameled wire being injured as the coil is inserted into the yoke to cause insulation failure.

SUMMARY OF THE INVENTION

It is an object of the present invention to solve the above-mentioned problems and to provide a brushless DC micromotor midget, highly efficient and good in workability in the process of manufacture.

According to the present invention, the above-mentioned problems can be solved by providing a brushless DC micromotor having the following characteristic construction. Namely, the invention relates to a brushless DC micromotor made up of a stator coil and a rotor housed inside thereof with magnet poles formed therein, which micromotor is characterized in that the stator coil is formed by coaxially winding more than one coil sheet formed on an insulating sheet, on which coil sheet a plurality of coil patterns are continuously provided in series in the direction of winding. According to the present invention, the stator coil of the brushless DC micromotor is formed by coaxially winding more than one coil sheet on an insulating sheet, on which coil sheet a plurality of coil patterns continuously formed in series, hence the micromotor of the present invention, unlike the conventional counterpart by the use of a copper wire coil, is space saving, having the advantage of being midget, thin and light.

Also, since the coil pattern is formed on a thin insulating sheet, the ratio of the volume of the coil conductor per unit space is increased and hence the motor's efficiency is largely improved, this enabling provision of a high-performance micromotor.

Further, since the stator coil can be made by coaxially winding the coil sheet with coil patterns formed thereon and it can be simply bonded in place inside the yoke, hence the workability in the process of manufacture is excellent and there is no risk of the insulation layer being injured as the stator coil is inserted in place. Moreover, it nicely fits inside the yoke, hence reduced is resistance and resulting heat generation in the running motor, this enabling provision of a high speed micromotor.

By way of describing embodiments of the present invention, reference is made to the accompanying drawings in which:

BRIEF DESCRIPTION OF THE DRAWINGS

FIG. 1 is a schematic vertical sectional view of a brushless DC micromotor of the present invention.

FIG. 2 is an illustrative view showing an example of the relative arrangement of the stator coil and the rotor.

DETAILED DESCRIPTION OF THE INVENTION

Figure 3:
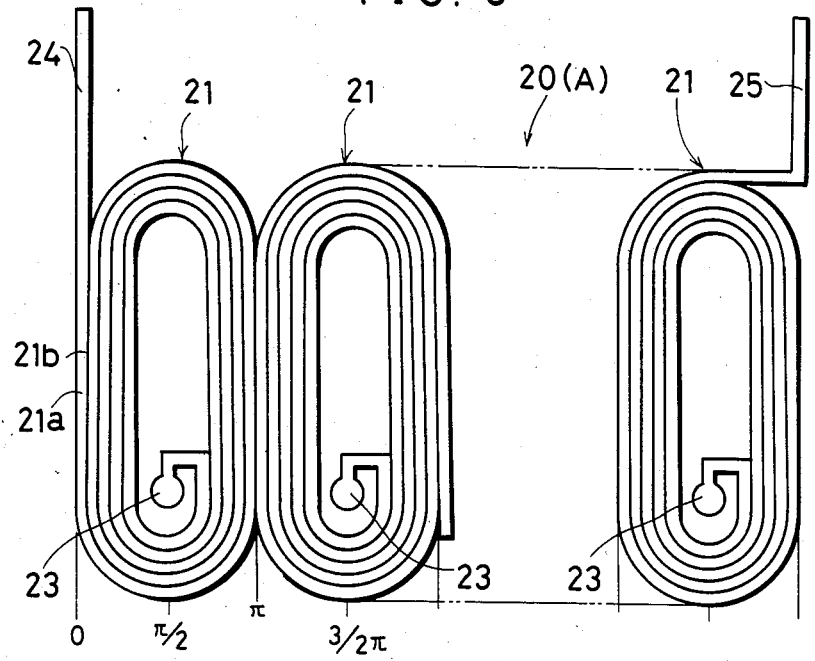
FIGS. 3 and 4 are the development elevations of coil sheets of A- and B-phase.

In these figures numeral 1 designates a yoke, 2 a stator coil, 3 a rotor having magnetic poles formed therein and 4 a revolving shaft respectively.

To describe the construction of a micromotor, a rotor 3 has set therethrough an integrally formed revolving shaft 4, which is held by bearings 6, at approximately the shaft center position of a cylindrical motor case 7. Outside the rotor 3 there is provided the stator coil 2, which is formed by coaxially winding coil sheets 20 (A) and 20 (B) representing coils of A-phase and B-phase.

A printed circuit board (PCB, not shown) having arranged thereon wirings supplying electric current to these coil sheets 20 (A) and 20 (B) and an element for detecting rotary angle of the rotor etc. is fitted to the inside of an end plate 5 closing the open end of the motor case 7.

The illustrated motor is a 2-phase one with 12 poles, as shown in FIG. 2, the rotor 3 has alternately arranged on the peripheral face thereof a total of 12 poles N and S, and at the same angular interval as these magnetic poles the A-and B-phase coil sheets 20 (A) and 20 (B) are wound with their coil patterns 21, 21 matching the respective magnetic poles of the rotor 3.

Figure 4:
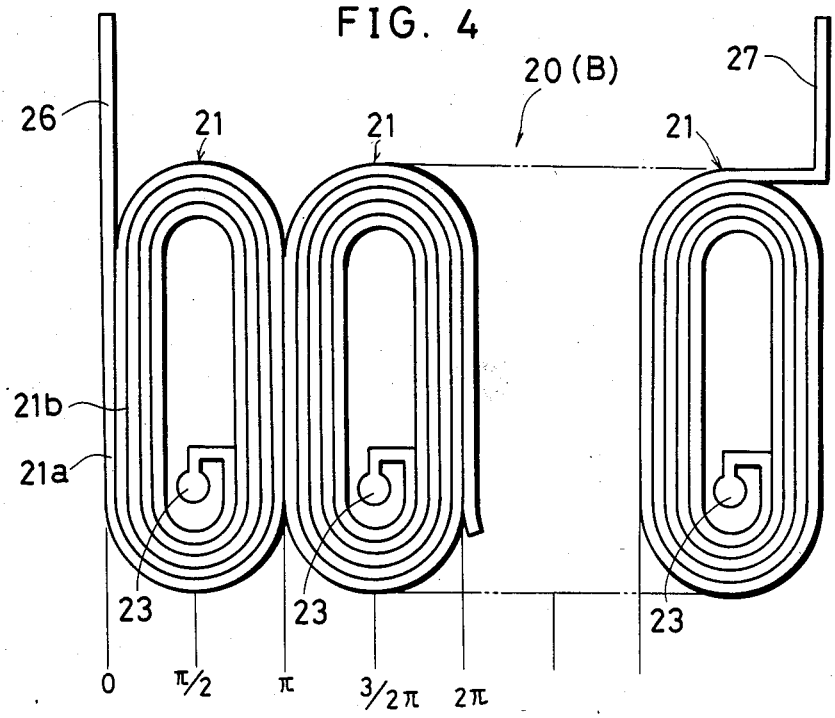
Figure 5:
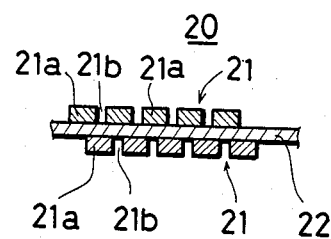
FIG. 5 is a partial sectional view of a coil sheet.

The coil patterns 21, 21 formed on A-phase coil sheet 20 (A) and B-phase coil sheet 20 (B) wound together coaxially are displaced half the coil pitch (90° in electric angle) as shown in the development elevations of FIGS. 3 and 4. FIGS. 3 and 4 show the development elevations of A- and B-phase coil sheets 20 (A) and 20 (B) (showing the surface only). Both coil sheets 20 (A) and 20 (B) are formed on both surface and back of the insulating sheet 22 with a plurality of coil patterns 21, 21 formed continuously, as shown in FIG. 5. The coil patterns 21, 21 provided on both surface and back of the insulating sheet 22 are connected in series with respective connecting terminals 23, 23 connected by means of through-holes or by brazing so that, when the coil pattern 21 is energized, magnetic fluxes formed by the coils of the surface coil pattern and by the coils of the back coil pattern are added to increase the density of magnet flux.

In FIGS. 3 and 4 numeral 24 designates the beginning terminal of A-phase coil, 25 the end terminal thereof, 26 the beginning terminal of B-phase coil and 27 the end terminal thereof.

It is for reinforcing the thin-walled coil sheet 20 that, as shown in FIG. 5, conductors 21a, 21a of the coil patterns 21, 21 formed on both surface and back of the coil sheet 20 are overlapped across the insulating sheet 22.

Figure 6:
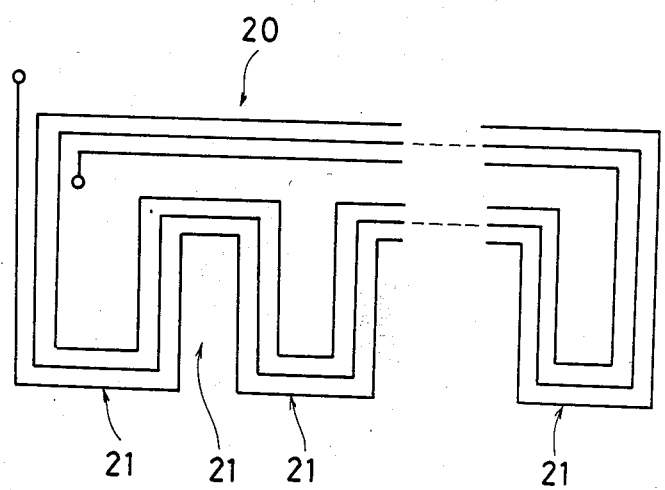
FIG. 6 is an illustrative view showing an example of a wavy coil pattern.

The coil sheet 20 is made by providing copper foil (not shown) on both a front surface and a back surface of the insulating sheet 22 and photo-etching (21b) the copper to foil to form the desired coil patterns. The form of the coil pattern 21, which is a vortex in FIGS. 3 and 4, may as well be rectangular wave-form as schematically shown in FIG. 6 or the like. (In FIG. 6 the coil pattern 21 is shown in solid line.) The A- and B-phase coil sheets 20 (A), 20 (B) having the coil patterns 21, 21 on both a front surface and a back surface of the insulating sheet 22 as mentioned above are wound coaxially with reasonable tightness lined with an insulating layer e.g. insulating film or insulating layer of adhesive (not shown) to form the stator coil 2 as shown in FIG. 2, and the stator coil 2 so formed is fixed inside the yoke 1 of the brushless DC micromotor by the use of an adhesive or the like as shown in FIG. 1.

In the above embodiment coil patterns are formed on both surface and back of the insulating sheet so as to increase the density of the magnetic fluxes formed by the stator coil. It is, however, also possible to have coil patterns formed on either surface or back of the insulating sheet, and in such a case the insulating layer used to line the coil sheet as it is wound is not necessary.

The above embodiments all deal with a case in which coil sheets are used to form a coil of two phases, namely A-phase and B-phase.

The present invention is, however, also applicable to cases where a coil of n-phase (n=3 or more) is formed, and in such a case a number of coil sheets equivalent to the number of phases of the coil are to be provided, the coil patterns are to be displaced from one another 180/n° in electric angle and the coil sheets are to be wound together with an insulating layer between adjacent laps.

Figure 7:
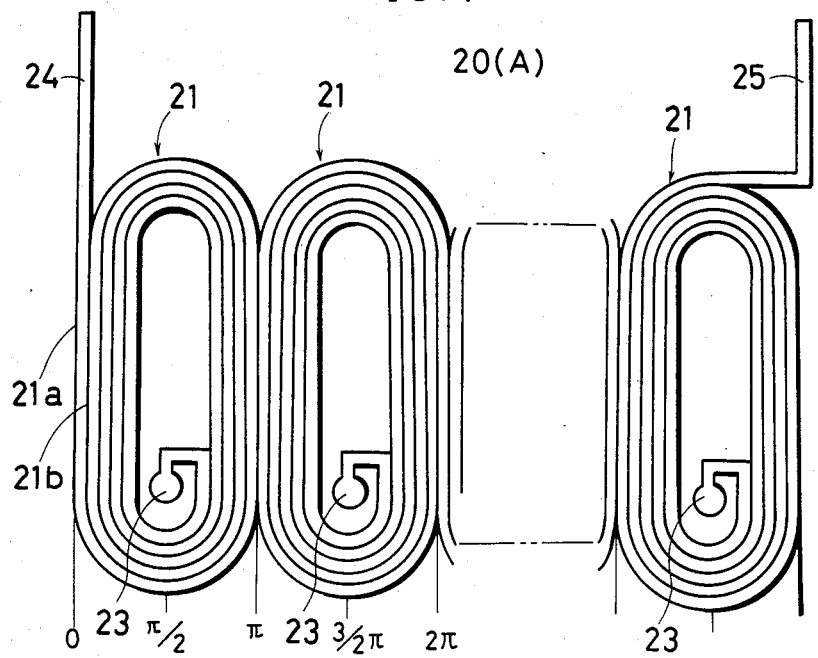
FIGS. 7 and 8 are the development elevations of coil sheets in other embodiments of the present invention.
Figure 8:
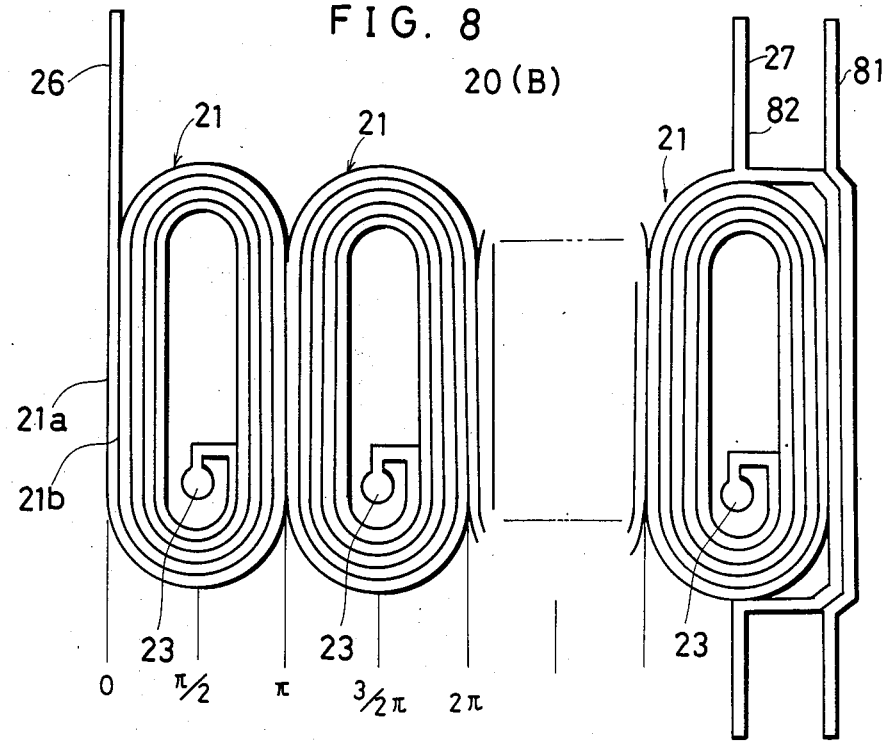

FIGS. 7 and 8 show another example of the coil sheet. In this example there are formed conductive patterns 81, 82 defining a transmission path for control signals different from the coil pattern 21 on the side of B-phase coil sheet 20 (B).

In forming such conductive patterns 81, 82, there shall be ensured safety from malfunction of the control means caused by electromotive forces induced therein.

For instance, when the conductive patterns as mentioned above are provided, the individual conductive patterns are bound to move in the rotating magnetic field formed by the rotor 3 when it is rotating, hence an electromotive force is induced in each conductive pattern. Hence, if there is a difference between the electromotive forces induced in the individual conductive patterns, a potential difference is caused between the individual conductive patterns, this causing malfunction of a control means for controlling other means such as lights and air and water feed. So, when, for instance, a transmission path for the control signals formed by the conductive patterns during rotation of the rotor 3 is opened, a potential difference is caused between the individual conductive patterns 81, 82, the resultant flow of electric current to the load giving cause for malfunction. (The indicator lamps, which should go off when energization is stopped, are possibly lit by formation of such potential differences.)

The condition for preventing such malfunction can be determined by application of Flemming's right-hand rule. That is, such condition can be easily provided if the conductive patterns 81, 82 are located equidistant from and at the same angle with respect to the center axis of the rotor 3, for, according to Flemming's right-hand law, the electromotive force e induced in a conductor moving in a magnetic field is defined by $e = Bl \cdot v \sin\Theta$ (where B is the magnetic flux density, l the length of conductor, v the revolving velocity and $\Theta$ the angle between magnetic field and conductor). To explain it further, since the magnetic flux B density depends on the angle $\Theta$ and the revolving velocity v depends on the distance r from the center axis of the rotor, $v = rw$, the electromotive force produced is substantially the same if the angle $\Theta$ as well as the distance r is approximately the same.

Hence, the above condition can be approximately satisfied with ease by providing the conductive patterns 81, 82 at the end of the coil pattern 21 formed on the coil sheet 20 in close proximity and in parallel or by arranging the conductive patterns so that they are overlapped layer after layer when the coil sheet is wound to form the stator coil 2.

Figure 9:
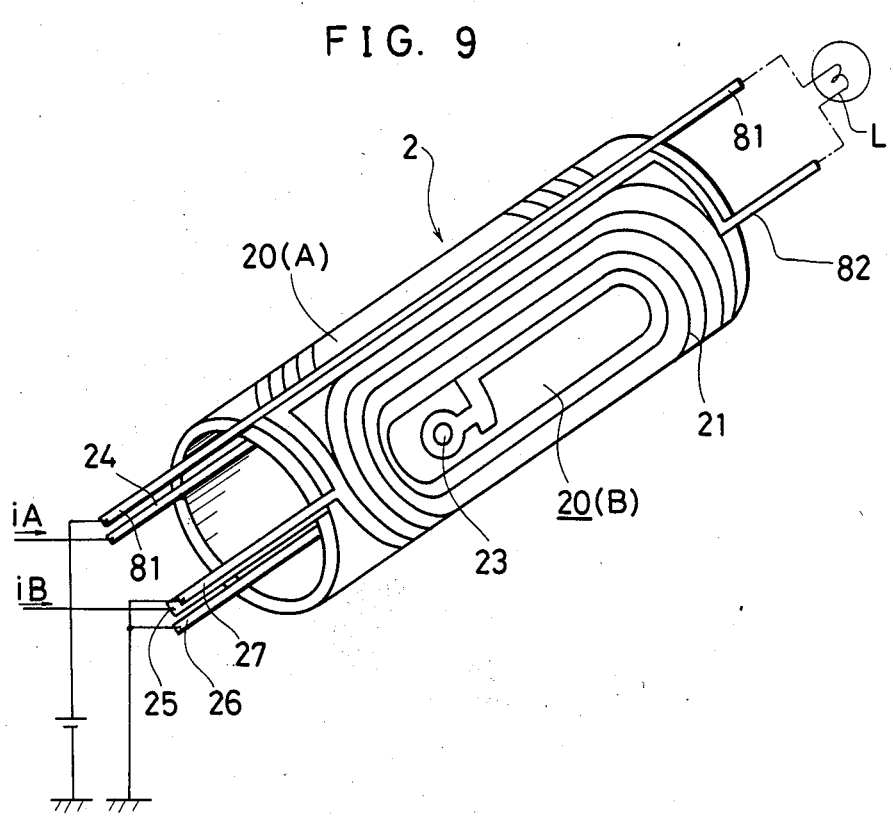
FIG. 9 is an illustrative view showing an example of wirings when a stator coil is made by winding the above coil sheet.

FIGS. 7 and 8 show development elevations for the coil sheet 20 (A) for A-phase and the coil sheet 20 (B) for B-phase, in which two conductive patterns 81, 82 are provided at one end of the coil pattern 21 on the coil sheet 20 (B) side, and the coil sheets are wound to form a stator coil so that the coil patterns 21, 21 are displaced by 90° (in electric angle) with respect to each other as shown in FIG. 2. FIG. 9 shows an example of wiring for the coil sheet in this case, and in the figure the end terminals 26 and 27 of the coil sheet 20 (B) of B-phase are in common with the conductive pattern 82 (ground), and at both ends of the conductive patterns 81, 82 are connected electric loads L such as lamps.

Figure 10:
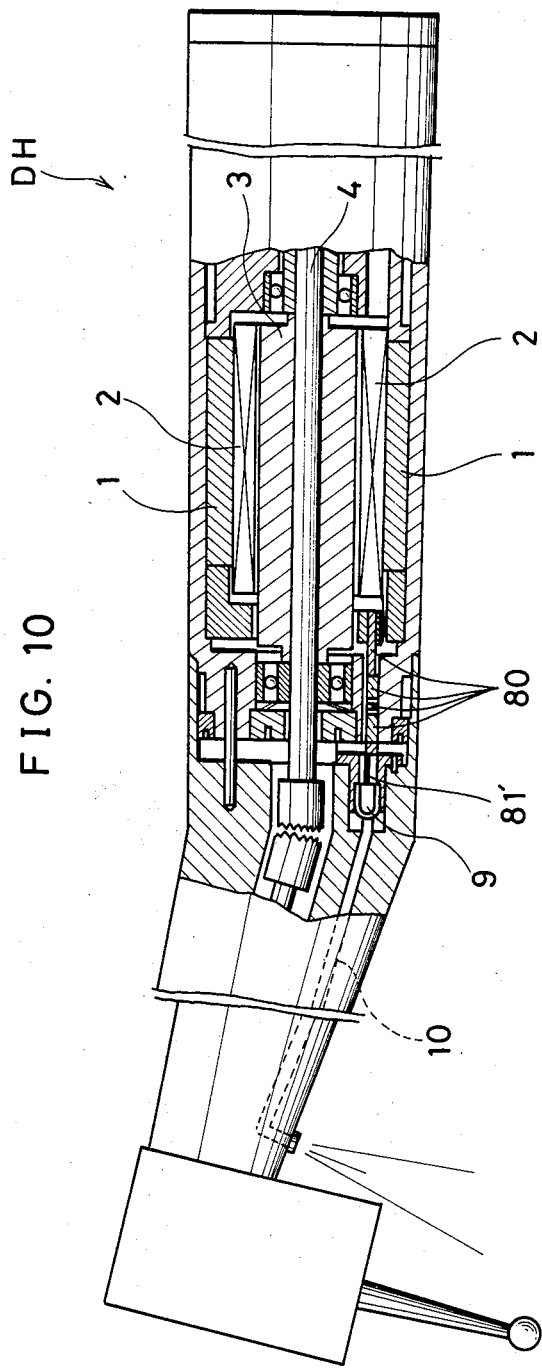
FIGS. 10 and 11 are partially cutaway vertical sectional front views of dental hand-pieces as embodiments of the present invention.
Figure 11:
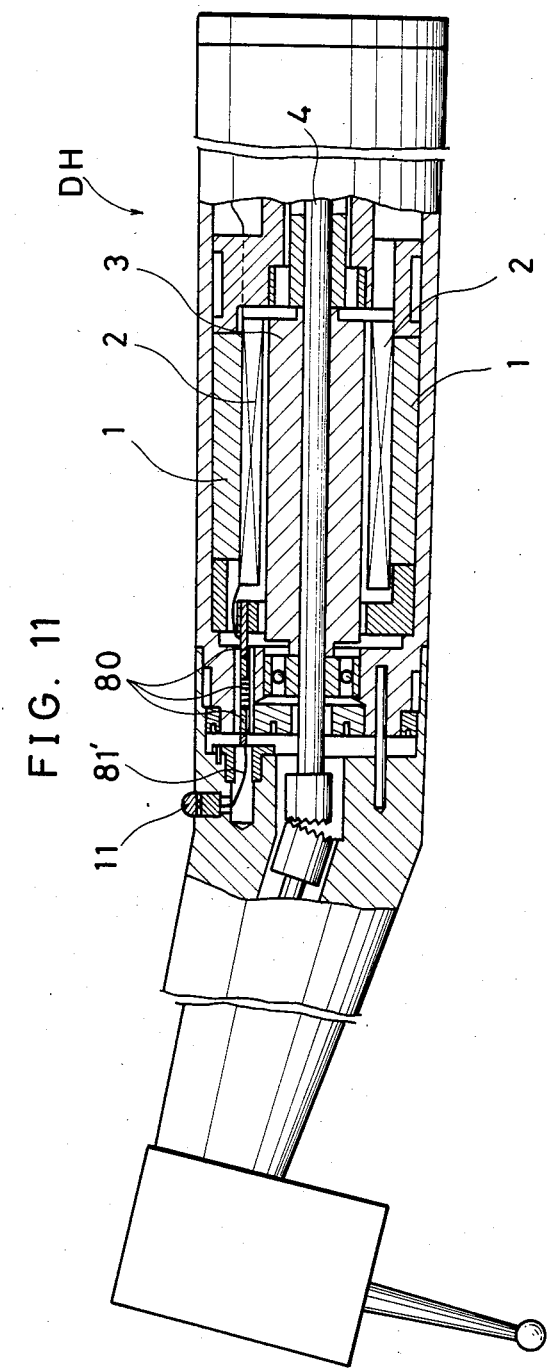

FIGS. 10 and 11 show respectively two examples of the brushless DC micromotor of the present invention whose stator coil is formed by winding coil sheets in which conductive patterns are arranged as shown above. FIG. 10 shows an example in which a brushless DC micromotor is built in a dental cordless handpiece DH, wherein numeral 1 designates a yoke, 2 a stator coil of the above-mentioned composition, 3 a rotor, 4 its revolving shaft and 81' a lead wire leading out of the micromotor with the other end thereof connected over an conductive member 80 to the conductive pattern 81 formed on one of the coil sheets 20 forming the stator coil 2 (the lead wire connected to the conductive pattern 82 is omitted), and in this embodiment it is so designed that electric current is supplied from the power source (not shown) provided behind the micromotor to LED 9 (light emitting diode) and the light emitted from LED 9 is transmitted via optical fiber 10 to the head of the handpiece DH to be projected through an opening provided at the base of the handpiece's head. FIG. 11 shows another example in which the brushless DC micromotor is built in the dental cordless handpiece DH. In this embodiment the lead wire 81' leading out of the micromotor with the other end thereof connected over the conductive member 80 to the conductive pattern 81 formed on one of the coil sheets 20 forming the stator coil 2 is used to form an energizing circuit for pushbutton-type control switches 11 provided on the front side of the handpiece DH. It is highly convenient for, with the control switches so arranged, the water feeder as well as the air feeder (not shown) can be ON/OFF controlled with the handpiece DH being manipulated by hand.

Although in the above embodiments are shown only examples in which a single transmission path is defined by two conductive patterns, it is, needless to say, possible to either increase the number of coil sheets or increase the number of conductive patterns formed on each coil sheet as necessary. Needless to say, however, it is desirous to satisfy the above-mentioned condition so as to prevent occurrence of a potential difference between the individual conductive patterns due to different inductive electromotive forces induced therein, which is bound to cause malfunction. Needless to say, the transmission path for control signals so formed is also useful for transmission of all sorts of other control signals.

Having described our invention as related to the embodiments shown in the accompanying drawings it is our intention that the invention be not limited by any of the details of description, unless otherwise specified, but rather be construed broadly within its spirit and scope as set out in the accompanying claims.

We claim:

1. A brushless DC micromotor made up of a stator coil and a rotor housed inside thereof with magnetic poles formed therein, said micromotor being characterized in that said stator coil comprises more than one coil sheet formed on an insulating sheet wound coaxially, on which coil sheet a plurality of coil patterns are continuously provided in series in the direction of winding and said coil sheet provides in addition to said coil patterns at least more than two conductive patterns defining a transmission path for control signals different from said coil patterns and the relative positional relationship between said conductive patterns satisfies the conditions that no potential difference is produced between said conductive patterns due to differences in electromotive force induced between said conductive patterns, and said conductive patterns being located equidistant from and at the same angle with respect to a center axis of the rotor.

* * * * *